United States Patent [19]

Blum et al.

[11] Patent Number: 4,876,339

[45] Date of Patent: Oct. 24, 1989

[54] PROCESS FOR SYNTHESIS OF AZACYCLOALKANE-2,2-DIPHOSPONIC ACIDS

[75] Inventors: Helmut Blum, Duesseldorf; Siglinde Hemmann, Meerbusch, both of Fed. Rep. of Germany

[73] Assignee: Henkel Kommanditgesellschaft auf Aktien, Duesseldorf, Fed. Rep. of Germany

[21] Appl. No.: 322,328

[22] Filed: Mar. 10, 1989

[30] Foreign Application Priority Data

Mar. 11, 1989 [DE] Fed. Rep. of Germany ....... 3808074

[51] Int. Cl.$^4$ .............................................. C07F 9/30
[52] U.S. Cl. .................... 540/450; 540/542; 546/21; 548/412
[58] Field of Search ................. 540/450, 542; 546/21; 548/412

[56] References Cited

U.S. PATENT DOCUMENTS

| | | | |
|---|---|---|---|
| 3,945,996 | 3/1976 | Conrad et al. | 540/527 |
| 3,988,443 | 10/1976 | Plöger et al. | 424/200 |
| 4,108,961 | 8/1978 | Ploger | 424/57 |
| 4,117,090 | 9/1978 | Ploger | 424/57 |
| 4,150,024 | 4/1979 | Syldatk et al. | 540/524 |

FOREIGN PATENT DOCUMENTS 2541981 3/1977 Fed. Rep. of Germany .
2343196 5/1979 Fed. Rep. of Germany .

Primary Examiner—Mukund J. Shah
Assistant Examiner—Miriam Sohn
Attorney, Agent, or Firm—Ernest G. Szoke; Wayne C. Jaeschke; Norvell E. Wisdom

[57] ABSTRACT

A reaction medium of ethanol condensed with 1–20, most preferably 4–6 moles, of ethylene or propylene oxide per mole of ethanol greatly improves the practicality of the preparation of azacycloalkane-2,2-diphosphonic acids of the general formula I:

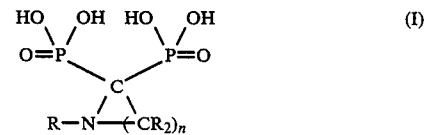

where R means a hydrogen or a lower alkyl radical with from 1 to 3 carbon atoms, and n means an integer between 3 and 11, by phosphonylating the corresponding lactams with phosphonic acid and phosphorous trihalides in the presence of water.

20 Claims, No Drawings

PROCESS FOR SYNTHESIS OF AZACYCLOALKANE-2,2-DIPHOSPONIC ACIDS

FIELD OF THE INVENTION

The present invention relates to a process for the preparation of azacycloalkane-2,2-diphosphonic acids and their salts by the reaction of lactams with a phosphonylating reagent and subsequent hydrolysis, with the optional conversion of the acids into their salts. The process uses a new reaction medium, in which the reaction can be carried out more readily and safely. The products are useful as sequestering agents, especially for alkaline earth metal ions, and as tartar inhibiting additives in toothpastes.

STATEMENT OF RELATED ART

The production of azacycloalkane-2,2-diphosphonic acids is described in the German Offenlegenschriften (DE-OS) No. 2 343 196 and 2 541 981. The former corresponds to U.S. Pat. Nos. 3,941,772 of Mar. 2, 1976 and 3,988,443 of Oct. 26, 1976, both to Plöger. Both processes start with lactams.

Plöger teaches melting the lactam, pure or mixed with phosphonic acid, then reacting the melt with phosphorus trichloride. These methods have not been commercialized because of difficult technical handling and a poor yield, which according to the figures in the patent amounts to 21% in making azacyclohexane-2,2-diphosphonic acid and 32% for azacycloheptane-2,2-diphosphonic acid. Also, because of the formation of decomposition products (predominantly polymeric phosphorus oxides and hydrides) after the hydrolysis of the reaction mixture, purification over activated carbon is needed. Because the azacycloalkane-2,2-diphosphonic acids are difficultly soluble and consequently often precipitate out after hydrolysis, purification must normally be accomplished via a soluble sodium salt. Pure free diphosphonic acids are regained from the purified salts by acidification.

According to DE-OS No. 2 541 981, the reaction of the lactam with phosphorus trichloride is carried out in a solvent, which in all the examples is chlorobenzene. Alternative solvents taught include diglymes, diglycol dimethyl ether, diethylene glycol dimethylether, dioxane, tetrachloroethane, tetrachloroethylene, trichloroethylene, α-chloronaphthalene, and high-boiling aliphatic and aromatic hydrocarbon mixtures.

The yield for azacycloheptane-2,2-diphosphonic acid by this process is given as 65 to 69.9%. However, this process also has considerable technical disadvantages. During the reaction, an inhomogeneous resinous reaction product is formed, which expands to 1.5 to 2 times the original reaction volume and forms a strong crust on the surface. As soon as this resinification occurs, the reaction product can no longer be stirred. Consequently, the reactor can initially be filled only to a third of its intended operating volume, and because of discontinuation of stirring, a considerably longer time is needed for hydrolysis and at the same time industrial safety problems occur. For example, as a result of local overheating, a strong emission of HCl can very rapidly occur.

Also, large amounts of orange-yellow colored phosphorus polymers are formed in this process, and also present industrial safety problems, as considerable amounts of poisonous and spontaneously inflammable phosphines are formed from these polymers during hydrolysis, or when the separated reaction matter is dissolved in caustic soda solution.

A major object of the present invention is to improve technically the methods known from the prior art, in particular so that (i) no substantial formation of foamed, insoluble, resinous reaction products occur while the reaction is being carried out, to prevent the reaction heat being dissipated by stirring, and (ii) the proportion of decomposition products, such as phosphorus polymers, formed during reaction is reduced, so as to reduce the hazard from phosphine formation during the subsequent hydrolysis.

DESCRIPTION OF THE INVENTION

Briefly, the object of the invention is achieved by using as an inert reaction medium or solvent alkoxylated alcohol adducts not previously used for such a purpose.

In the more detailed description of the invention below, except in the operating examples, all numbers used to describe amounts of materials or reaction conditions are to be understood as modified by the term "about".

The invention constitutes a method for the production of azacycloalkane-2,2-diphosphonic acids of the general formula I:

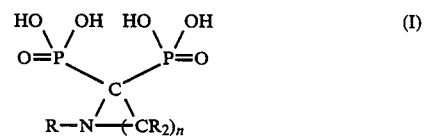

where R means a hydrogen or a lower alkyl radical with from 1 to 3 carbon atoms and n means an integer between 3 and 11, or of a water soluble salt of an acid of formula I, by reaction of a lactam of the general formula II:

where R and n have the same meanings as for formula (I), with a phosphorus trihalide and phosphonic acid in the presence of water in an inert reaction medium, and processing during and after reaction in a manner known per se, including the possible conversion of the acids formed into their salts by reaction with a suitable base. The invention is characterized by use as inert solvent of a material having the chemical structure of an adduct of ethanol with from 1 to 20 moles of ethylene oxide or propylene oxide per molecule of ethanol adducted. The solvent need not actually be made from ethanol as a starting material. Sometimes it is more convenient to begin with a higher molecular weight material, such as ethyl diglycol, also called diethylene glycol monoethyl ether. Any product made by condensing a given number of moles of ethylene oxide with ethanol can usualy also be made by condensing two fewer moles of ethylene oxide with ethyl diglycol, for example.

By the use of this type of adduct as a reaction medium, the reaction mixture of lactam, phosphonic acid, and phosphorus trihalide, remains totally fluid throughout the entire duration of the reaction, and therefore can be continuously stirred, so that the constituents of the reactive medium can be varied in a wide range. As a consequence of this, the reaction product can be hydrolyzed without the problems encountered in prior art uses of a different inert solvent for this reaction. Moreover, surprisingly, the formation of the unwanted yellow-orange decomposition products observed in the prior art also does not occur with this solvent if sufficient amounts of it are used. Thus the danger of phosphine formation is avoided. Furthermore there is the resulting advantage that free pure diphosphonic acids can be directly separated from the reaction product after the hydrolysis with water. The purification stage via the sodium salt, usually in the form of the di-sodium salts, may thus be eliminated.

An adduct of ethanol with from 1 to 10 mole of epoxide, or as particularly preferred, with from 4 to 6 mole of epoxide is used to advantage. These adducts are normally obtained in a manner known in the art (cf., e.g., G. Dieckelmann and H. Heinz, *The Basics of Industrial Oleochemistry* (Peter Pomp GmbH, Essen (West Germany), 1988), pp. 104–107), by the reaction of ethanol or an alkoxylated ethanol, such as ethyl diglycol, with appropriate amounts of ethylene oxide or propylene oxide.

The amount of adduct used as reaction medium is not critical. It is preferably limited, for maximum economy, to the amount above which a further dilution of the initial mixture of reactants no longer shows a rise in yield. On the other hand, however, even when smaller amounts of reaction medium are used, there is no resinification and foaming of the reaction product. The intended reactor capacity can therefore be fully used at the outset.

The concentrations of yellow-colored decomposition products formed during processes according to this invention are low. Continuous industrial processing is thus not hindered by such decomposition products, even if purification via the alkali salt is desired. In any case there is considerable saving of time. If a high-purity product is not required, it is normally not necessary with the process according to the invention to carry out any purification via the alkali salt, because the low polymer formation minimizes the amount of impurity present.

Use of such an adduct as a reaction medium is particularly suitable for synthesis of azacyclopentane-2,2-diphosphonic acid, azacyclohexane-2,2-diphosphonic acid, azacycloheptane-2,2-diphosphonic acid, azacyclooctane-2,2diphosphonic acid, and their salts, with phosphorus trichloride used as the phosphorus trihalide.

Additionally it is possible for a worker skilled in the art, by varying the amount and content of the reaction medium, to optimize the synthesis process in such a way, that either pure diphosphonic acid can be isolated in a direct manner, or the direct production of alkali salts can be achieved, as in many cases the di-sodium salt form of azacycloheptane diphosphonic acid, for example, is desired.

The process according to the invention may be further appreciated from, but is not to be limited by, the operating examples given below.

EXAMPLE 1

Initially, 495 g phosphorus trichloride was added drop by drop into a mixture of 226 g of caprolactam, 167.4 g of 98% phosphonic acid, 64 g of water and 870 g of a reaction medium prepared by condensing ethyl diglycol with an average of 2.3 moles of ethylene oxide per mole of ethyl diglycol. (This reaction medium is abbreviated hereinafter as "EDG+2.3EO".) The reaction mixture was cooled from the outside during the reaction. The temperature of the reaction mixture reached a maximum of 45° C. After the addition of the phosphorus trichloride ended, the reaction mixture was heated to 110° C. over two hours and then stirred for a further two hours. Throughout the entire reaction time the reaction mixture remained easy to stir. As a result of the absence of a resinous reaction product, the voluminous formation of foam also did not occur.

After cooling, the reaction product was dissolved with 1 liter of water and heated for a short time to boiling point for complete hydrolysis. The di-phosphonic acid was precipitated in the form of a white crystalline powder. This was drawn off by suction after cooling, washed chloride-free with water, and finally again with ethanol. After drying 300.4 g (58% of the theoretical yield) of pure azacycloheptane-2,2-diphosphonic acid, with the formula $C_6H_{15}NO_6P_2$ and corresponding molar mass of 259.0, was obtained. Elemental analysis showed 27.6% C found (calculated 27.8), 5.93% H found (calculated 5.79), 23.7% P found (calculated 23.9), and 5.29% N (calculated 5.41). Titration with sodium hydroxide solution indicated a molar mass of 259.9 after titrating 1 equivalent and of 260.1 after titrating 2 equivalents.

EXAMPLE 2

A mixture of 226 g caprolactam, 167.4 g of 98% phosphonic acid, and 64 g water were mixed in 400 g of EDG+2.3EO and reacted with 495 g phosphorus trichloride as in example 1 and heated to 120° C. Throughout the following reaction time of 2.5 hours the reaction product remained easy to stir. A small amount of yellow-orange colored decomposition product was formed. For this reason the diphosphonic acid obtained after hydrolysis was separated from the remainder of the reaction products and medium. The crude acid was suspended in 1 liter of water for the purpose of further purification, the water was adjusted with 50% sodium hydroxide solution to a pH value of 8.5, and the undissolved polymer products were separated by the addition of activated carbon, with all suspended solids eventually separated from the remaining solution by filtration. After acidification of the resulting salt solution with concentrated hydrochloric acid up to pH 1, the difficultly soluble azacycloheptane-2,2-diphosphonic acid was separated off. Yield: 331.5 g, or 64% of theoretical. Elemental analysis showed: % C found 27.7 (calculated 27.8), % H found 5.95 (calc. 5.79), % P found 23.8 (calc. 23.9), % N found 5.34 (calc. 5.41). Titration with sodium hydroxide indicated a molar mass of 261.2 after 1 equivalent had been neutralized and 260.7 after 2 equivalents.

EXAMPLE 3

This used the same amounts of the same ingredients as examples 1 and 2, except for using 580 g of EDG+2.3EO as reaction medium. The reaction temperature reached 120° C. The synthesis mixture could be stirred without problems throughout the entire reaction time. Because of the formation of a small amount of phosphorus polymer products, the diphosphonic acid was purified during the salt stage, as in Example 2. (The formation of decomposition products was, even so, considerably less here than in a synthesis with, for example, diglyme as the solvent). Yield: 321.2 g, or 62% of theoretical. Elemental analysis showed: % C found 27.9 (calculated 27.8), % H found 5.86 (calc. 5.79), % P 23.7 found (calc. 23.9), % N found 5.28 (calc. 5.41). Titration with sodium hydroxide solution indicated a molar mass of 260.8 after 1 equivalent had been titrated and 261.4 after 2 equivalents.

COMPARATIVE EXAMPLE 1

The same amounts of the same ingredients as in Examples 1-3 were used, except that the reaction medium was 290 g of diethylene glycol dimethyl ether; no adduct according to the invention was used. The reaction mixture was heated to 120° C. and left for two and a half hours at this temperature. During this afterheating, the reaction product became resinous and stirring had to be suspended. During the same time, a large amount of yellow-orange colored decomposition product formed. After the hydrolysis, the impure diphosphonic acid was separated and the highly yellow-orange colored filter cake—as described in example 2—was dissolved and/or suspended in caustic soda solution for separation purposes. The azacycloheptane-2,2-diphosphonic acid was isolated in free form by acidification with hydrochloric acid. The yield amounted to 260.5 g or 50.3% of theoretical. Elemental analysis showed: % C found 27.7 (calculated 27.8), % H found 5.89 (calc. 5.79), % P found 23.7 (calc. 23.9), % N found 5.31 (calc. 5.41). Titration with sodium hydroxide solution indicated a molar mass of 259.8 after 1 equivalent had been titrated and 260.1 after 2 equivalents.

EXAMPLE 4

495 g phosphorus trichloride were added drop by drop into a mixture of 226 g caprolactam, 167.4 g of 98% phosphonic acid, 24 g of water, and 600 g of EDG+2.3EO while being cooled. The temperature rose during this addition to approximately 45° C. and was then increased within 2 hours to 120° C. When the final temperature was reached, a strong pasty reaction product and small amounts of colored decomposition products had been formed. In this example stirring was suspended; however, the unwanted foaming of the reaction mixture did not occur. (If the stirring is continued, the stirrer stirs itself free, and therefore the reaction product can no longer be moved.) The reaction mixture was kept for 1.5 hours at 120° C., cooled to 50° to 60° C., and a further 40 g of water was added drop by drop. After this, the reaction mixture was re-heated to 120° C. and left at this temperature. The reaction mixture was thus kept for 2.5 hours in total at 120° C. After this the cooled reaction product was hydrolysed with 1 liter of water and the azacycloheptane-2,2-diphosphonic acid, precipitated in the form of a crystalline powder, was separated. Yield was 393.7 g or 76% of theoretical. Elemental analysis showed: % C found 27.9 (calculated 27.8), % H found 5.91 (calc. 5.79), % N found 5.27 (calc. 5.41), % P found 23.7 (calc. 23.9). Titration with sodium hydroxide solution indicated a molar mass of 262.9 after 1 equivalent had been titrated and 259.7 after 2 equivalents.

(Note: In the specification and the claims, "phosphonic acid" is specified as a reaction component. This is the same material as is probably more commonly named "phosphorous acid", but according to IUPAC rule 5.214 it should be named as "phosphonic acid".)

What is claimed is:

1. A process for the preparation of azacycloalkane-2,2-diphosphonic acids of the general formula I:

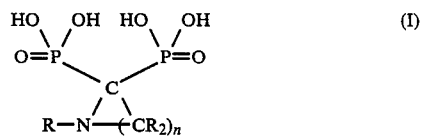

where R means a hydrogen or a lower alkyl radical with from 1 to 3 carbon atoms, and n means an integer between 3 and 11, or of a water soluble salt of an acid of formula I, said process comprising reacting a lactam of the general formula II:

where R and n have the same meanings as for formula (I), with a phosphorus trihalide and phosphonic acid in the presence of water in an inert reaction medium that has the chemical structure of an adduct of ethanol with an average of from about 1 to about 20 moles of ethylene oxide or propylene oxide per mole of ethanol.

2. A process according to claim 1, characterized in that the adduct used as the reaction medium has the chemical structure made by condensing ethanol with an average of about 1 to about 10 moles of epoxide.

3. A process according to claim 2, wherein the adduct used as the reaction medium has the chemical structure made by condensing ethanol with an average of about 4 to about 6 moles of epoxide.

4. A process according to claim 3, characterized in that the reaction medium is made by adducting ethanol or ethyl diglycol with ethylene oxide.

5. A process according to claim 2, characterized in that the reaction medium is made by adducting ethanol or ethyl diglycol with ethylene oxide.

6. A process according to claim 1, characterized in that the reaction medium is made by adducting ethanol or ethyl diglycol with ethylene oxide.

7. A process according to claim 6, in which the primary product is azacyclopentane-2,2-diphosphonic acid, azacyclohexane-2,2-diphosphonic acid, azacycloheptane-2,2-diphosphonic acid, azacyclooctane-2,2-diphosphonic acid, or a salt of one of these acids.

8. A process according to claim 5, in which the primary product is azacyclopentane-2,2-diphosphonic acid, azacyclohexane-2,2-diphosphonic acid, azacycloheptane- 2,2-diphosphonic acid, azacyclooctane-2,2-diphosphonic acid, or a salt of one of these acids.

9. A process according to claim 4, in which the primary product is azacyclopentane-2,2-diphosphonic acid, azacyclohexane-2,2-diphosphonic acid, azacycloheptane-2,2-diphosphonic acid, azacyclooctane-2,2-diphosphonic acid, or a salt of one of these acids.

10. A process according to claim 3, in which the primary product is azacyclopentane-2,2-diphssphonic acid, azacyclohexane-2,2-diphosphonic acid, azacycloheptane-2,2-diphosphonic acid, azacyclooctane-2,2-diphosphonic acid, or a salt of one of these acids.

11. A process according to claim 2, in which the primary product is azacyclopentane-2,2-diphosphonic acid, azacyclohexane-2,2-diphosphonic acid, azacycloheptane-2,2-diphosphonic acid, azacyclooctane-2,2-diphosphonic acid, or a salt of one of these acids.

12. A process according to claim 1, in which the primary product is azacyclopentane-2,2-diphosphonic acid, azacyclohexane-2,2-diphosphonic acid, azacycloheptane-2,2-diphosphonic acid, azacyclooctane-2,2-diphosphonic acid, or a salt of one of these acids.

13. A process according to claim 12, wherein the amount of reaction medium used is sufficiently large that no byproduct capable of producing gaseous phosphines upon hydrolysis is formed.

14. A process according to claim 11, wherein the amount of reaction medium used is sufficiently large that no byproduct capable of producing gaseous phosphines upon hydrolysis is formed.

15. A process according to claim 6, wherein the amount of reaction medium used is sufficiently large that no byproduct capable of producing gaseous phosphines upon hydrolysis is formed.

16. A process according to claim 5, wherein the amount of reaction medium used is sufficiently large that no byproduct capable of producing gaseous phosphines upon hydrolysis is formed.

17. A process according to claim 4, wherein the amount of reaction medium used is sufficiently large that no byproduct capable of producing gaseous phosphines upon hydrolysis is formed.

18. A process according to claim 3, wherein the amount of reaction medium used is sufficiently large that no byproduct capable of producing gaseous phosphines upon hydrolysis is formed.

19. A process according to claim 2, wherein the amount of reaction medium used is sufficiently large that no byproduct capable of producing gaseous phosphines upon hydrolysis is formed.

20. A process according to claim 1, wherein the amount of reaction medium used is sufficiently large that no byproduct capable of producing gaseous phosphines upon hydrolysis is formed.

* * * * *